United States Patent
Towson et al.

(10) Patent No.: US 9,630,967 B2
(45) Date of Patent: Apr. 25, 2017

(54) PROCESS FOR MAKING ZILPATEROL

(71) Applicant: Intervet Inc., Madison, NJ (US)

(72) Inventors: James C. Towson, Flemington, NJ (US); Shing-Chun Wong, Union, NJ (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/652,585

(22) PCT Filed: Dec. 17, 2013

(86) PCT No.: PCT/EP2013/076850
§ 371 (c)(1),
(2) Date: Jun. 16, 2015

(87) PCT Pub. No.: WO2014/095822
PCT Pub. Date: Jun. 26, 2014

(65) Prior Publication Data
US 2015/0315195 A1  Nov. 5, 2015

Related U.S. Application Data

(60) Provisional application No. 61/738,438, filed on Dec. 18, 2012.

(51) Int. Cl.
*C07D 487/04* (2006.01)
*C07D 487/06* (2006.01)

(52) U.S. Cl.
CPC ......... *C07D 487/04* (2013.01); *C07D 487/06* (2013.01)

(58) Field of Classification Search
CPC ................................................... C07D 487/04
See application file for complete search history.

(56) References Cited

U.S. PATENT DOCUMENTS

| | | | |
|---|---|---|---|
| 4,585,770 A | 4/1986 | Frechet et al. | |
| 4,900,735 A | 2/1990 | Grandadam | |
| 5,731,028 A | 3/1998 | Chevremont et al. | |
| 5,847,124 A | 12/1998 | Chevremont et al. | |

FOREIGN PATENT DOCUMENTS

| | | |
|---|---|---|
| WO | 2008006828 A1 | 1/2008 |
| WO | 2008044127 A1 | 4/2008 |
| WO | 2008050207 A1 | 5/2008 |
| WO | 2008092924 A1 | 8/2008 |
| WO | 2008119754 A1 | 10/2008 |
| WO | 2010070004 | 6/2010 |

OTHER PUBLICATIONS

PCT International Search Report corresponding to PCT/EP2013/076850, mailed on Apr. 4, 2015 (3 Pages).
Hunger et al., Benzimidazol-Derivate and verwandte Heterocyclen VII 1) Synthese neuer 2-Amino-benzimidazole, Helv. Chim. Acta., 1961, pp. 1273-1282, vol. 44; No. 158-159. In German-Translation to be provided later.
Meth-Cohn, et al., N- Bridged Heterocycles. Part 5.1 a,w- Bis-(2-oxobenzimidazolinyl) -alkanes and -ethers as Selective Ligands for Group-1 and -2 Metals, J. Chem. Soc. Perkin Trans. 1, 1982, pp. 261-270.

*Primary Examiner* — Brian McDowell

(57) ABSTRACT

This invention generally relates to processes for making zilpaterol and salts thereof, as well as processes for making intermediates that, interalia, may be used to make zilpaterol and salts thereof.

13 Claims, No Drawings

PROCESS FOR MAKING ZILPATEROL

CROSS-REFERENCE TO RELATED APPLICATIONS

This application is a national stage entry under 35 U.S.C. §371 of PCT/EP2013/076850, filed on Dec. 17, 2013, which claims priority to U.S. Provisional Application No. 61/738,438, filed on Dec. 18, 2012. The content of PCT/EP2013/076850 is hereby incorporated by reference in its entirety.

BACKGROUND

Zilpaterol is a β-adrenergic agonist used as a feed additive for cattle at slaughter age that has been shown to increase their average daily gain. U.S. Pat. No. 4,900,735 describes zootechnical compositions of racemic trans zilpaterol and its derivatives can be used to increase the rate of weight gain, improve the feed efficiency and increase carcass leanness in livestock, poultry and fish.

Methods for making zilpaterol are known in the art. For example, in U.S. Pat. No. 4,585,770, Fréchet et al. discuss compounds encompassed by a genus characterized as 6-amino-7-hydroxy-4,5,6,7-tetrahydro-imidazo[4,5,1-jk][1]-benzazepin-2(1H)-one derivatives and pharmaceutically acceptable acid addition salts thereof. The derivatives correspond in structure to the following formula:

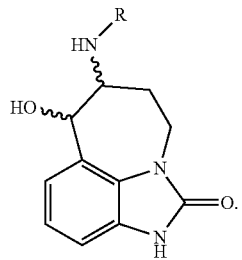

Here, R can be various substituents, and the wavy lines indicate that the bonds to the 6-amino and 7-OH groups have the trans configuration. This genus encompasses racemic trans zilpaterol when R is isopropyl.

The methods reported in U.S. Pat. No. 4,585,770 use 4,5-dihydro-imidazo[4,5,1-jk][1]benzazepin-2,6,7(1H)-trione-6-oxime as an intermediate. This compound corresponds to the following structure:

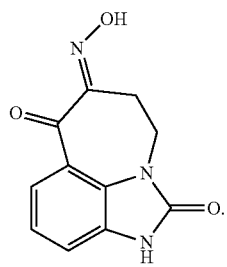 [SMILES: O=C1/C(=N/O)CCn2c(=O)[nH]c3cccc1c32]

As indicated in U.S. Pat. No. 4,585,770, 4,5-dihydro-imidazo[4,5,1-jk][1]benzazepin-2,6,7(1H)-trione-6-oxime may be formed from starting materials that have been long known in the art. U.S. Pat. No. 4,585,770 illustrates the use of two such starting materials. In both examples, the starting materials are used to form 5,6-dihydro-imidazo[4,5,1-jk][1]benzazepin-2,7-(1H,4H)-dione, which, in turn, may be used to make 4,5-dihydro-imidazo[4,5,1-jk][1]benzazepin-2,6,7 (1H)-trione-6-oxime.

In one of the examples in U.S. Pat. No. 4,585,770, the starting material is 1,3-dihydro-1-(1-methylethenyl)-2H-benzimidazol-2-one, which is described in *J. Chem. Soc. Perkins*, p. 261 (1982):

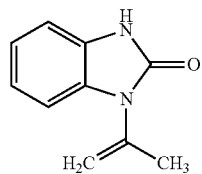

1,3-dihydro-1-(1-methylethenyl)-2H-benzimidazol-2-one

U.S. Pat. No. 4,585,770 indicates that 1,3-dihydro-1-(1-methylethenyl)-2H-benzimidazol-2-one may be reacted with an alkyl 4-halobutyrate (i.e., $R^A$—$(CH_2)_3$—$COOR^B$ (wherein $R^A$ is Cl, Br, or I; and $R^B$ is $C_1$-$C_4$-alkyl), such as methyl or ethyl 4-bromobutyrate) and a base (e.g., an alkali metal) to form a butanoate, which, in turn may be hydrolyzed with an acid (e.g., $H_2SO_4$) in an alkanol (e.g., methanol or ethanol) to remove the methylethenyl substituent. The hydrolysis product then may be subjected to saponification by reacting it with a base (e.g., NaOH or KOH) in an alkanol to form a carboxylic acid. Subsequently, the carboxylic-acid-terminated side chain may be cyclized to form 5,6-dihydro-imidazo[4,5,1-jk][1]benzazepin-2,7-[1H,4H]-dione by reacting the carboxylic acid with thionyl chloride to obtain a chloride, and then treating the chloride with a Lewis acid (e.g., aluminum chloride) in an organic solvent (e.g., methylene chloride or dichloroethane):

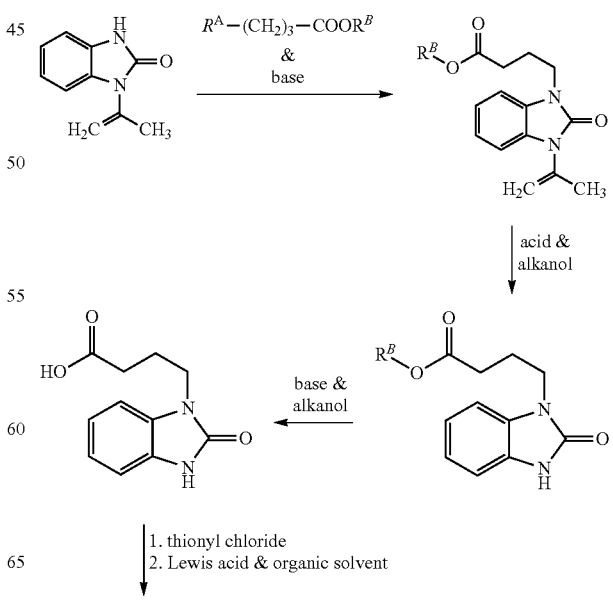

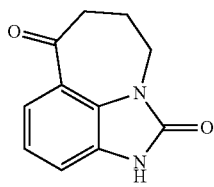

dihydro-imidazo[4,5,1-jk][1]
benzazepin-2,7(1H,4H)-dione

See U.S. Pat. No. 4,585,770, col. 4, line 3 to col. 5, line 14; and Example 14, col. 12, lines 1-68.

In another example in U.S. Pat. No. 4,585,770, the starting material is 1,3-dihydro-1-benzyl-2H-benzimidazol-2-one, which is described in *Helv.*, Vol 44, p. 1278 (1961):

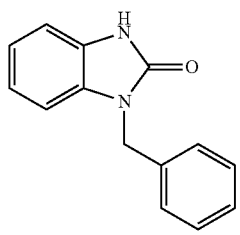

1,3-dihydro-1-benzyl-2H-
benzimidazol-2-one

U.S. Pat. No. 4,585,770 indicates that the 1,3-dihydro-1-benzyl-2H-benzimidazol-2-one may be reacted with ethyl 4-bromobutyrate and sodium hydride to form 1,3-dihydro-2-oxo-3-benzyl-1H-benzimidazol-1-butanoate, which, in turn may be subjected to saponification by reacting it with methanolic NaOH to form 1,3-dihydro-2-oxo-3-benzyl-1H-benzimidazol-1-butanoic acid. The butanoic acid side chain may then be cyclized by reacting the 1,3-dihydro-2-oxo-3-benzyl-1H-benzimidazol-1-butanoic acid with thionyl chloride to obtain a chloride, and then treating the chloride with aluminum chloride in dichloroethane. The cyclized product, in turn, may be hydrolyzed using o-phosphoric acid in phenol to form 5,6-dihydro-imidazo[4,5,1-jk][1]benzazepin-2,7-[1H,4H]-dione. See U.S. Pat. No. 4,585,770, Example 1, Steps A-D, col. 6, line 10 to col. 7, line 35.

Using the methods reported in U.S. Pat. No. 4,585,770, 5,6-dihydro-imidazo[4,5,1-jk][1]benzazepin-2,7-[1H,4H]-dione may be reacted with an alkyl nitrite (e.g., tert-butyl nitrite or isoamyl nitrite), in the presence of a base or acid (e.g., HCl), to form 4,5-dihydro-imidazo[4,5,1-jk][1]benzazepin-2,6,7[1H]-trione-6-oxime. The 4,5-dihydro-imidazo[4,5,1-jk][1]benzazepin-2,6,7[1H]-trione-6-oxime, in turn, is reduced via catalytic hydrogenation (with, for example, hydrogen in the presence of palladium on carbon) and/or sodium borohydride to form racemic 6-amino-7-hydroxy-4,5,6,7-tetrahydro-imidazo[4,5,1-jk][1]-benzazepin-2[1H]-one:

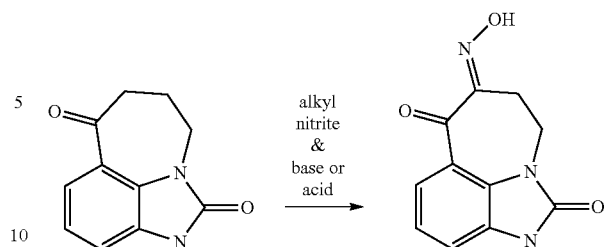

dihydro-imidazo[4,5,1-jk][1]
benzazepin-2,7(1H,4H)-
dione 4,5-dihydro-imidazo[4,5,1-jk]
[1] benzazepin-2,6,7(1H)-
trione-6-oxime catalytic hydrogenation
and/or
sodium borohydride

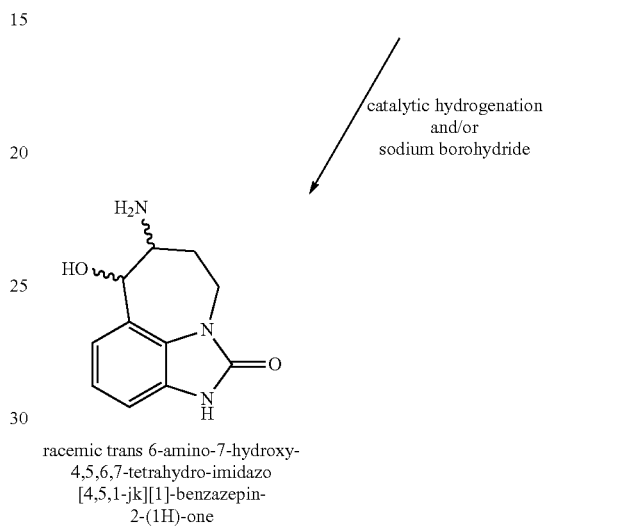

racemic trans 6-amino-7-hydroxy-
4,5,6,7-tetrahydro-imidazo
[4,5,1-jk][1]-benzazepin-
2-(1H)-one In the illustrative example in U.S. Pat. No. 4,585,770, the 4,5-dihydro-imidazo[4,5,1-jk][1]benzazepin-2,6,7[1H]-trione-6-oxime is converted into racemic trans 6-amino-7-hydroxy-4,5,6,7-tetrahydro-imidazo[4,5,1-jk][1]-benzazepin-2[1H]-one in two steps: the 4,5-dihydro-imidazo[4,5,1-jk][1]benzazepin-2,6,7[1H]-trione-6-oxime is first reacted with $H_2$ in the presence of Pd on carbon, and, then, after filtration, the hydrogenation product is reacted with sodium borohydride. See U.S. Pat. No. 4,585,770, col. 2, line 50 to col. 4, line 2; and Example 1, Steps E & F, col. 7, line 38 to col. 8, line 3.

U.S. Pat. No. 4,585,770 reports that the trans stereoisomers of 6-amino-7-hydroxy-4,5,6,7-tetrahydro-imidazo[4,5,1-jk][1]-benzazepin-2 [1H]-one may be alkylated with acetone in the presence of a reducing agent (e.g., an alkali metal borohydride or cyanoborohydride, such as sodium cyanoborohydride) to form racemic trans zilpaterol:

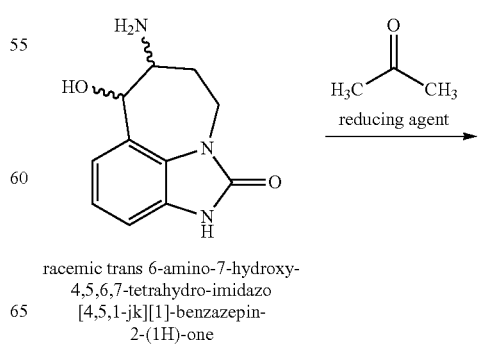

racemic trans 6-amino-7-hydroxy-
4,5,6,7-tetrahydro-imidazo
[4,5,1-jk][1]-benzazepin-
2-(1H)-one reducing agent

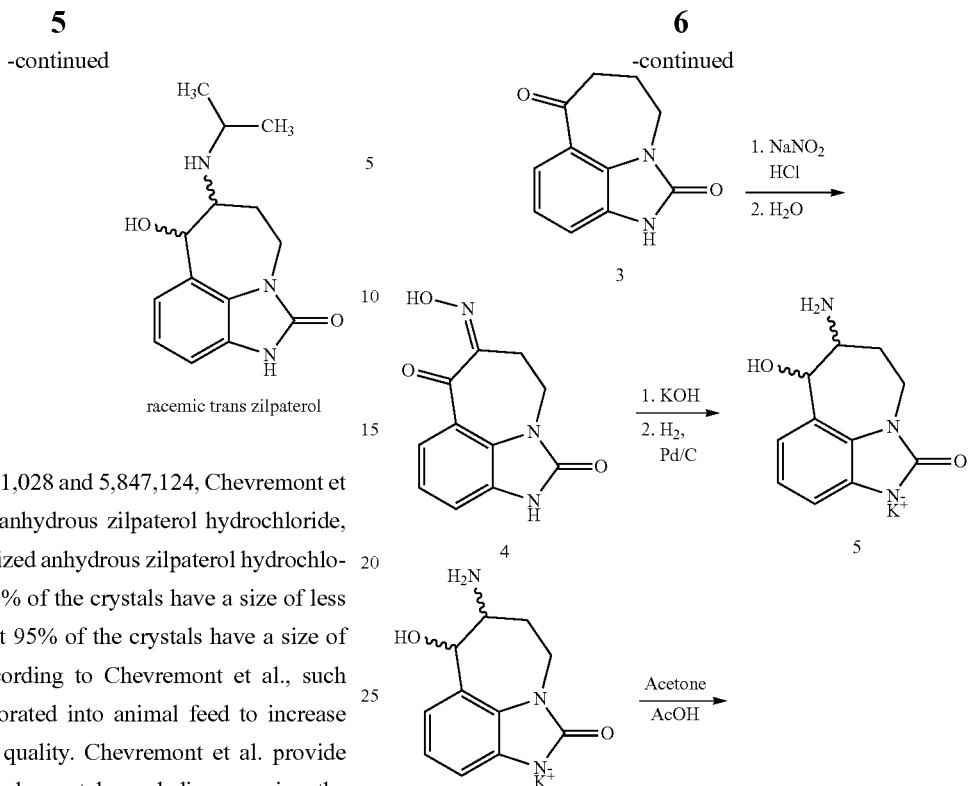

racemic trans zilpaterol

In U.S. Pat. Nos. 5,731,028 and 5,847,124, Chevremont et al. discuss crystallized anhydrous zilpaterol hydrochloride, and particularly crystallized anhydrous zilpaterol hydrochloride wherein less than 5% of the crystals have a size of less than 15 μm, and at least 95% of the crystals have a size of less than 250 μm. According to Chevremont et al., such crystals may be incorporated into animal feed to increase body weight and meat quality. Chevremont et al. provide methods for making such crystals, and discuss using the crystals to make animal premixes in which the crystals are secured to a corn cob support having a greater particle size. They also discuss monohydrate and trihydrate intermediates that can be useful in, for example, making the crystals.

WO 2008/119754 discloses a process to make zilpaterol as shown in Scheme 1 below

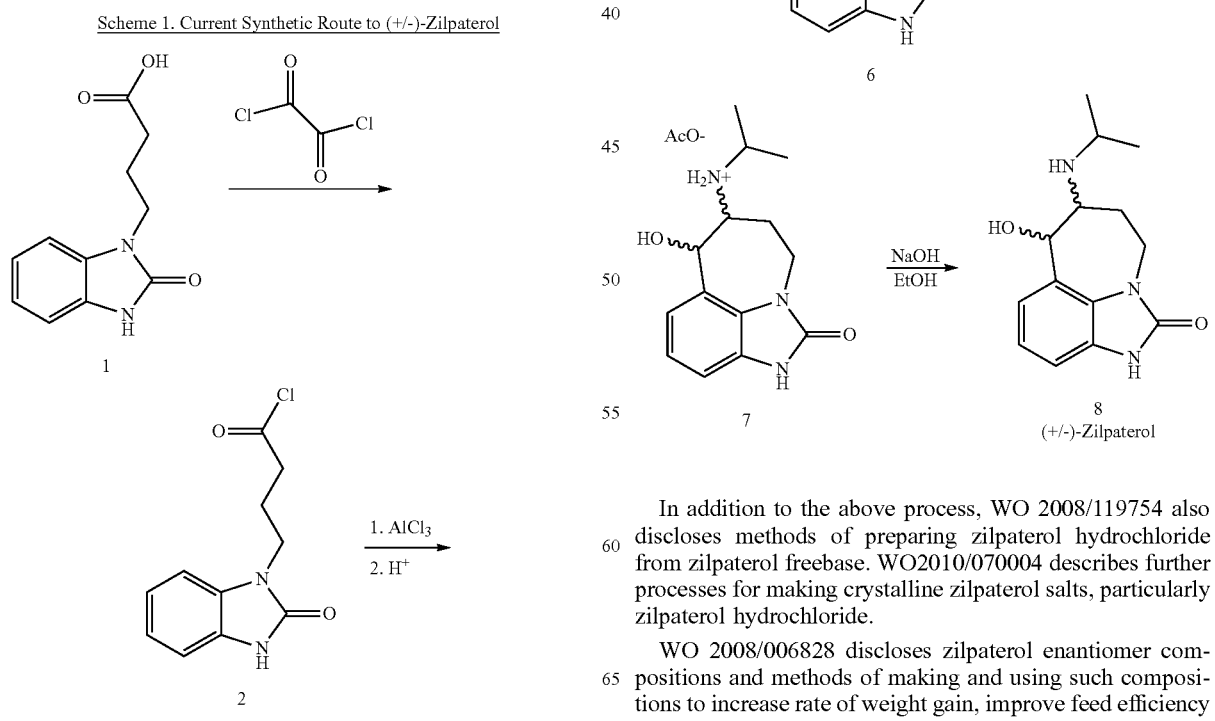

In addition to the above process, WO 2008/119754 also discloses methods of preparing zilpaterol hydrochloride from zilpaterol freebase. WO2010/070004 describes further processes for making crystalline zilpaterol salts, particularly zilpaterol hydrochloride.

WO 2008/006828 discloses zilpaterol enantiomer compositions and methods of making and using such compositions to increase rate of weight gain, improve feed efficiency and increase carcass leanness in livestock, poultry and fish.

In WO 2008/092924, the enantioselective synthesis of zilpaterol and intermediates is disclosed.

WO 2008/044127 discloses non zilpaterol beta-2-adrenocreptor agonists and methods of their preparation.

Alternative process intermediates have been envisioned herein that could shorten the zilpaterol production process and lower manufacturing cost.

SUMMARY OF THE INVENTION

An embodiment of the invention is a method of preparing a compound of Formula I or a salt thereof

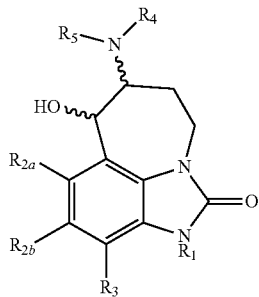

I comprising:
a. reacting a compound of Formula II

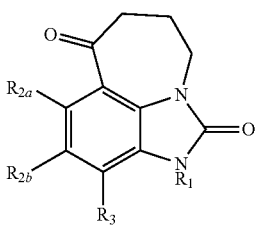

II with a halogenating agent to produce a compound of Formula III

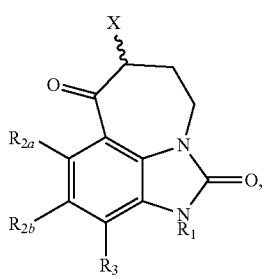

III wherein X is Cl, Br, or I;

b. reacting compound III with a compound of Formula A

A to produce a compound of Formula IV;

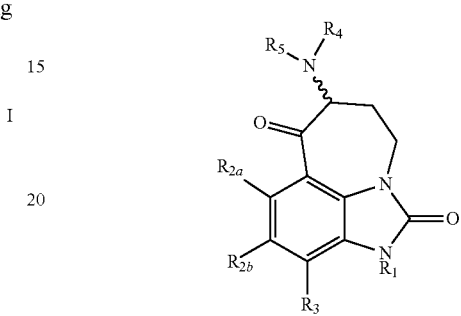

IV and
c. reacting compound IV with a reducing agent to produce a compound of Formula I wherein:

$R_1$ is selected from hydrogen, amino, alkyl, alkenyl, alkynyl, aryl, benzyl, or any cyclic version or heteroatom containing version thereof and wherein for each alkyl, alkenyl, alkynyl, aryl, benzyl, and any cyclic version or heteroatom containing version may be substituted or unsubstituted;

$R_{2a}$ and $R_{2b}$ are the same or different and are each independently selected from hydrogen, halogen, hydroxyl, amino, alkyl, alkenyl, alkynyl, aryl, benzyl, alkoxy, alkylthioxy, alkyl sulfonyl, alkyl sulfoxy, alkyl thio or any cyclic version or hetero atom containing version thereof and wherein for each alkyl, alkenyl, alkynyl, aryl, benzyl, alkoxy, alkylthioxy, alkyl sulfonyl, alkyl sulfoxy, alkyl thio and any cyclic version or heteroatom containing version may be substituted or unsubstituted;

$R_3$ is selected from hydrogen, halogen, hydroxyl, amino, alkyl, alkenyl, alkynyl, aryl, benzyl, alkoxy, alkylthioxy, alkyl sulfonyl, alkyl sulfoxy, alkyl thio or any cyclic version or heteroatom containing version thereof and wherein for each alkyl, alkenyl, alkynyl, aryl, benzyl, alkoxy, alkylthioxy, alkyl sulfonyl, alkyl sulfoxy, alkyl thio and any cyclic version or heteroatom containing version may be substituted or unsubstituted; and $R_4$ and $R_5$ are independently selected from hydrogen, amino, alkyl, alkenyl, alkynyl, aryl, benzyl, or any cyclic version or heteroatom containing version thereof and wherein for each alkyl, alkenyl, alkynyl, aryl, benzyl, and any cyclic version or heteroatom containing version may be substituted or unsubstituted.

In another embodiment, $R_4$ and $R_5$ may be taken together to form a cyclic substituent. This cyclic substituent may be aromatic or non aromatic and may further include one or more additional hetero atoms selected from O, S and N.

In another embodiment, the reducing agent is $NaBH_4$

In another embodiment, $R_1$-$R_3$ and $R_5$ are hydrogen. In another embodiment, $R_4$ is isopropyl.

In another embodiment, the zilpaterol is zilpaterol hydrochloride.

DETAILED DESCRIPTION

The present invention relates to certain process improvements that are envisioned over current preparations of zilpaterol. Process improvement would help to satisfy the production of larger quantities of zilpaterol at a reduced price. The present invention also relates to process for making zilpaterol analogs of Formula (I) wherein $R_1$-$R_5$ are defined below. Finally, the present invention relates to novel compounds which are intermediates in the process.

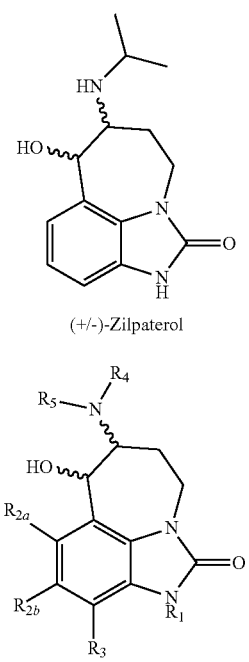

(+/−)-Zilpaterol

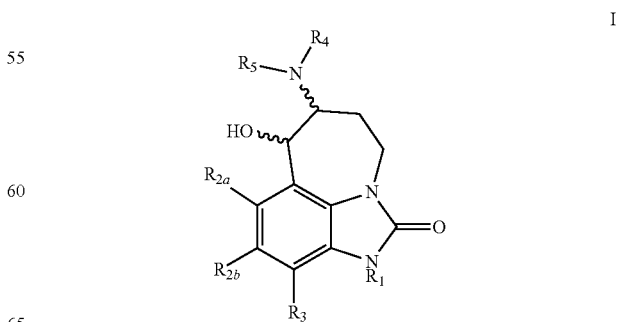

I

Scheme 2 provides a summary of the improved process. Specifically, beginning with ketone 3, alternative routes have been employed to expedite the synthesis of (+/−)-zilpaterol.

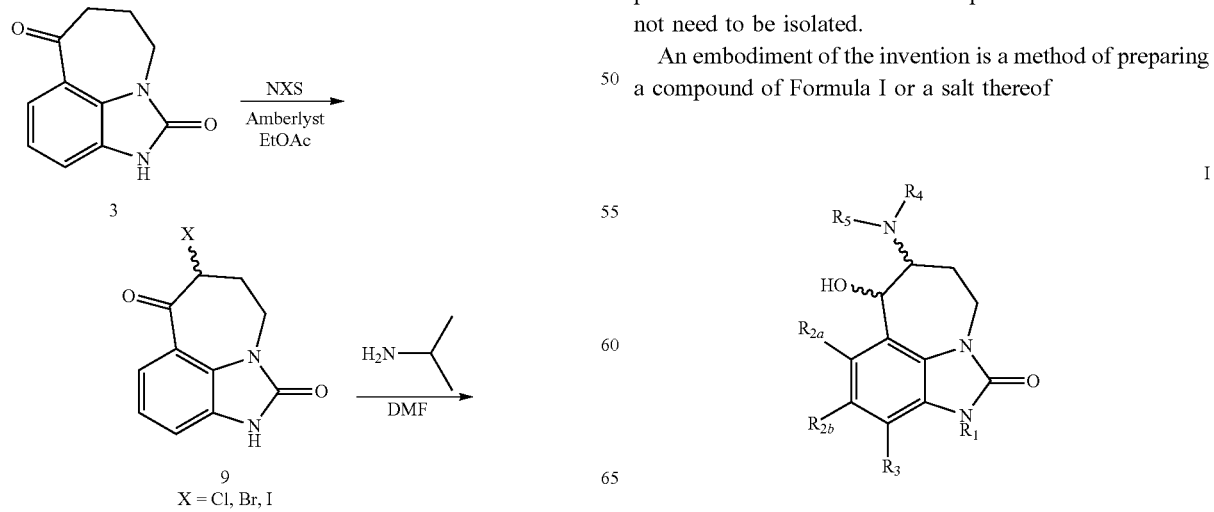

Scheme 2. Synthesis of (+/−)-zilpaterol from Ketone 3

Beginning with the synthesized Compound 3, from Scheme 1, an a-halogenation using, for example, N-chlorosuccinimide (NCS), N-bromosuccinimide (NBS), N-iodosuccinimide (NIS), bromine or iodine is employed to provide Intermediate 9 wherein X=Cl, Br or I. The a-halogenation of ketones with NCS, NBS, and NIS is a well-known and efficient reaction in organic chemistry. However, this reaction has never been documented with the (+/−)-zilpaterol process, and it offers significant improvement relative to the current manufacturing method. Towards this end, the chemistry leading to the bromide version of this molecule (9, X=Br) has been reduced to practice in 65% yield. A nucleophilic substitution of the halide from 9 using, for example, inexpensive isopropylamine afforded Compound 10. A hydride reduction of the ketone in 10 completed the new process and delivered (+/−)-zilpaterol (8). Possible reducing agents for this final step can include but are not limited to sodium borohydride, potassium borohydride, lithium aluminum hydride and borane-tetrahydrofuran complex. The displacement followed by reduction of the a-aminoketone, 10, gave a $^1$H NMR spectrum that contained a very distinct signal near 4 ppm, which is characteristic of (+/−)-zilpaterol. In an embodiment, the reactions from compound 9 to compound 10 and from compound 10 to compound 8 are conducted in situ. Compound 10 can be but does not need to be isolated.

An embodiment of the invention is a method of preparing a compound of Formula I or a salt thereof

I comprising:

a. reacting a compound of Formula II

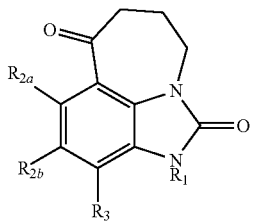

with a halogenating agent to produce a compound of Formula III

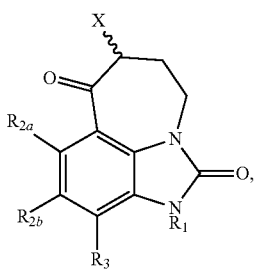

wherein X is Cl, Br, or I;

b. reacting compound III with a compound of Formula A

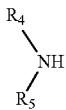

to produce a compound of Formula IV;

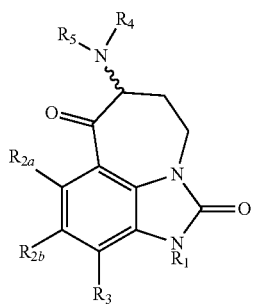

and c. reacting compound IV with a reducing agent to produce a compound of Formula I wherein:

$R_1$ is selected from hydrogen, amino, alkyl, alkenyl, alkynyl, aryl, benzyl, or any cyclic version or heteroatom containing version thereof and wherein for each alkyl, alkenyl, alkynyl, aryl, benzyl, and any cyclic version or heteroatom containing version may be substituted or unsubstituted;

$R_{2a}$ and $R_{2b}$ are the same or different and are each independently selected from hydrogen, halogen, hydroxyl, amino, alkyl, alkenyl, alkynyl, aryl, benzyl, alkoxy, alkylthioxy, alkyl sulfonyl, alkyl sulfoxy, alkyl thio or any cyclic version or heteroatom containing version thereof and wherein for each alkyl, alkenyl, alkynyl, aryl, benzyl, alkoxy, alkylthioxy, alkyl sulfonyl, alkyl sulfoxy, alkyl thio and any cyclic version or heteroatom containing version may be substituted or unsubstituted;

$R_3$ is selected from hydrogen, halogen, hydroxyl, amino, alkyl, alkenyl, alkynyl, aryl, benzyl, alkoxy, alkylthioxy, alkyl sulfonyl, alkyl sulfoxy, alkyl thio or any cyclic version or heteroatom containing version thereof and wherein for each alkyl, alkenyl, alkynyl, aryl, benzyl, alkoxy, alkylthioxy, alkyl sulfonyl, alkyl sulfoxy, alkyl thio and any cyclic version or heteroatom containing version may be substituted or unsubstituted; and $R_4$ and $R_5$ are independently selected from hydrogen, amino, alkyl, alkenyl, alkynyl, aryl, benzyl, or any cyclic version or heteroatom containing version thereof and wherein for each alkyl, alkenyl, alkynyl, aryl, benzyl, and any cyclic version or heteroatom containing version may be substituted or unsubstituted.

In another embodiment, $R_4$ and $R_5$ may be taken together to form a cyclic substituent. This cyclic substituent may be aromatic or non aromatic and may further include one or more additional hetero atoms selected from O, S and N.

In an alternative embodiment, $R_1$ is selected from $C_{1-10}$ alkyl, $C_{2-10}$ alkenyl, $C_{3-10}$ alkynyl, or any cyclic version or heteroatom containing version thereof and wherein for each $C_{1-10}$ alkyl, $C_{2-10}$ alkenyl, $C_{3-10}$ alkynyl, and any cyclic version or heteroatom containing version may be substituted or unsubstituted;

In an alternative embodiment, $R_{2a}$ and $R_{2b}$ are each independently selected from $C_{1-10}$ alkyl, $C_{2-10}$ alkenyl, $C_{3-10}$ alkynyl, $C_{1-10}$ alkoxy, $C_{1-10}$ alkylthioxy, $C_{1-10}$ alkyl sulfonyl, $C_{1-10}$ alkyl sulfoxy, $C_{1-10}$ alkyl thio or any cyclic version or heteroatom containing version thereof and wherein for each $C_{1-10}$ alkyl, $C_{2-10}$ alkenyl, $C_{3-10}$ alkynyl, $C_{1-10}$ alkoxy, $C_{1-10}$ alkylthioxy, $C_{1-10}$ alkyl sulfonyl, $C_{1-10}$ alkyl sulfoxy, $C_{1-10}$ alkyl thio and any cyclic version or heteroatom containing version may be substituted or unsubstituted;

In an alternative embodiment, $R_3$ is selected from $C_{1-10}$ alkyl, $C_{2-10}$ alkenyl, $C_{3-10}$ alkynyl, $C_{1-10}$ alkoxy, $C_{1-10}$ alkylthioxy, $C_{1-10}$ alkyl sulfonyl, $C_{1-10}$ alkyl sulfoxy, $C_{1-10}$ alkyl thio or any cyclic version or heteroatom containing version thereof and wherein for each $C_{1-10}$ alkyl, $C_{2-10}$ alkenyl, $C_{3-10}$ alkynyl, $C_{1-10}$ alkoxy, $C_{1-10}$ alkylthioxy, $C_{1-10}$ alkyl sulfonyl, $C_{1-10}$ alkyl sulfoxy, $C_{1-10}$ alkyl thio and any cyclic version or heteroatom containing version may be substituted or unsubstituted; and In an alternative embodiment, $R_4$ and $R_5$ are independently selected from $C_{1-10}$ alkyl, $C_{2-10}$ alkenyl, $C_{3-10}$ alkynyl, or any cyclic version or heteroatom containing version thereof and wherein for each $C_{1-10}$ alkyl, $C_{2-10}$ alkenyl, $C_{3-10}$ alkynyl, and any cyclic version or heteroatom containing version may be substituted or unsubstituted.

In an embodiment, the reactions from compound III to compound IV and from compound IV to compound I are conducted in situ. Compound IV is not isolated.

In an embodiment, the halogenating agent is selected from N-chlorosuccinimide (NCS), N-bromosuccinimide (NBS), N-iodosuccinimide (NIS), bromine and iodine.

In an embodiment, the reducing agent is selected from sodium borohydride, potassium borohydride, lithium aluminum hydride and borane-tetrahydrofuran complex.

In another embodiment, the reducing agent is $NaBH_4$

In another embodiment, $R_1$-$R_3$ and $R_5$ are hydrogen. In another embodiment, $R_4$ is isopropyl.

In another embodiment, the zilpaterol is zilpaterol hydrochloride.

Alternative suitable salts generally include acid addition salts. In general, an acid addition salt can be prepared by reacting the zilpaterol free base with an approximately stoichiometric amount of an inorganic or organic acid. Examples of often suitable inorganic acids for making pharmaceutically acceptable salts include hydrobromic, hydroiodic, nitric, carbonic, sulfuric, and phosphoric acid. Examples of often suitable organic acids for making pharmaceutically acceptable salts generally include, for example, aliphatic, cycloaliphatic, aromatic, araliphatic, heterocyclic, carboxylic, and sulfonic classes of organic acids. Specific examples of often suitable organic acids include cholate, sorbate, laurate, acetate, trifluoroacetate (or "CF$_3$COOH" or "TFA"), formate, propionate, succinate, glycolate, gluconate, digluconate, lactate, malate, tartaric acid, citrate, ascorbate, glucuronate, maleate, fumarate, pyruvate, aspartate, glutamate, aryl carboxylic acid (e.g., benzoate), anthranilic acid, mesylate, stearate, salicylate, p-hydroxybenzoate, phenylacetate, mandelate, embonate (pamoate), alkylsulfonate (e.g., ethanesulfonate), arylsulfonate (e.g., benzenesulfonate), pantothenate, 2-hydroxyethanesulfonate, sulfanilate, cyclohexylaminosulfonate, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate. In some such embodiments, for example, the salt comprises a trifluoroacetate, mesylate, or tosylate salt.

In one embodiment, the invention is a method of preparing zilpaterol comprising:

a. reacting a compound of Formula 3

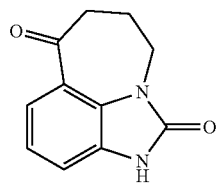

3 with a halogenating agent to produce a compound of Formula 9

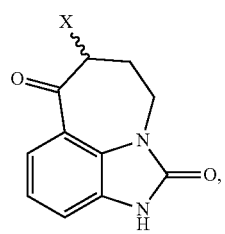

9 wherein X is Cl, Br, or I;

b. reacting compound 9 with a compound of Formula A

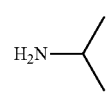

A to produce a compound of Formula 10;

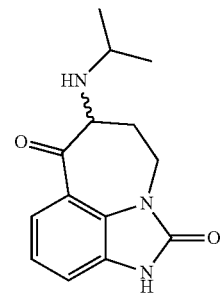

10 and c. reacting compound 10 with reducing agent to produce zilpaterol.

In another embodiment, the halogenating agent is is selected from N-chlorosuccinimide (NCS), N-bromosuccinimide (NBS), N-iodosuccinimide (NIS), bromine and iodine.

In another embodiment, the reducing agent is selected from sodium borohydride, potassium borohydride, lithium aluminum hydride and borane-tetrahydrofuran complex.

In another embodiment, the reducing agent is NaBH$_4$

In another embodiment, this route may be used to produce zilpaterol analogs. See Formula (Ia) below. This route can be amenable to a variety of R substituents (see Formula (II)), thereby permitting the preparation of derivatives of zilpaterol. In an alternative embodiment, R$_1$ may be affixed throughout any stage of the synthesis. In yet another embodiment, the R$_2$ s may be the same or different. In a further embodiment, the R$_2$ s may be affixed preceding preparation of Compound 1 in Scheme 1. Examples of R$_1$, may be selected from among but are not limited to hydrogen, alkyl, alkenyl, alkynyl, aryl, benzyl, and any cyclic version or heteroatom containing version thereof. R$_{2a}$ and R$_{2b}$ and R$_3$ may be selected from among but are not limited to hydrogen, halogen, alkyl, alkenyl, alkynyl, aryl, benzyl, alkoxy, alkylthioxy, and any cyclic version or heteroatom containing version thereof. In each R, the alkyl, alkenyl, alkynyl, aryl, benzyl, alkoxy, alkylthioxy, and any cyclic version or heteroatom containing version may be substituted or unsubstituted.

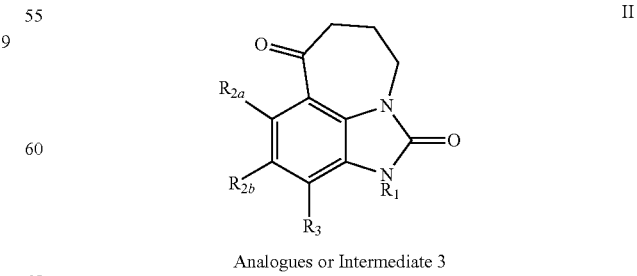

II

Analogues or Intermediate 3
Formula (II)

Scheme 3. Synthesis of analogues of zilpaterol (Formula I) from the ketone of Formula II Scheme 4. Alternative routes where the amino group is initially added unsubstituted and then the substitution is added either prior to or after the reduction of the ketone to an alcohol. $R_1$ to $R_3$ are defined as above.

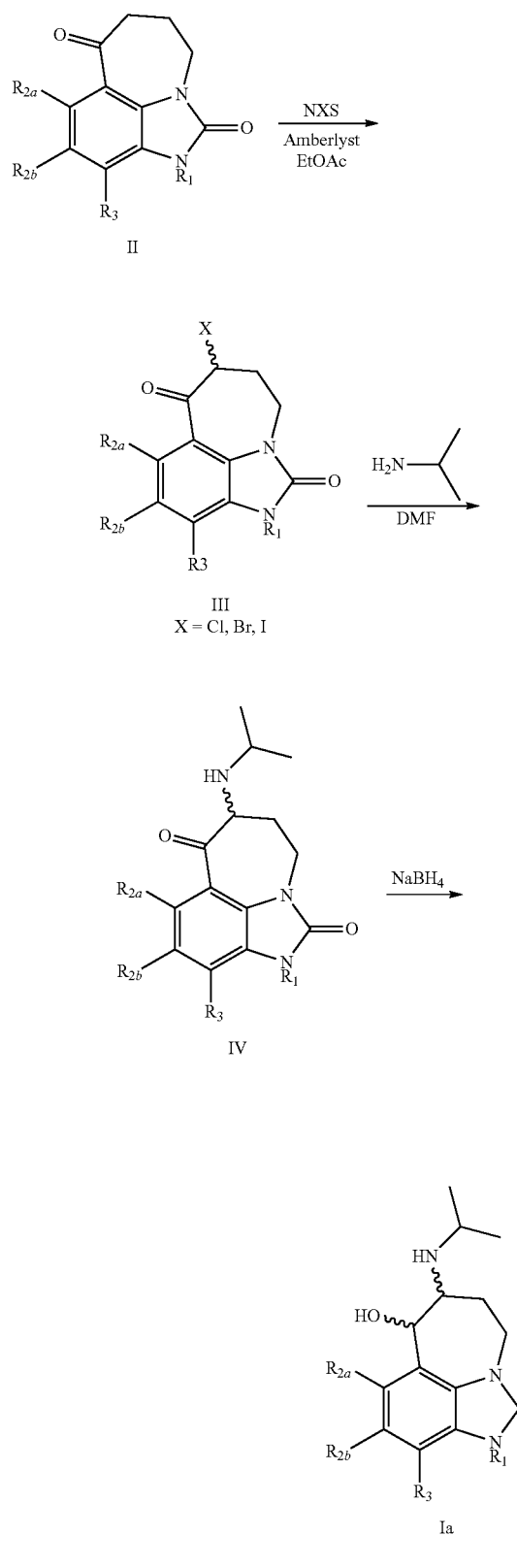

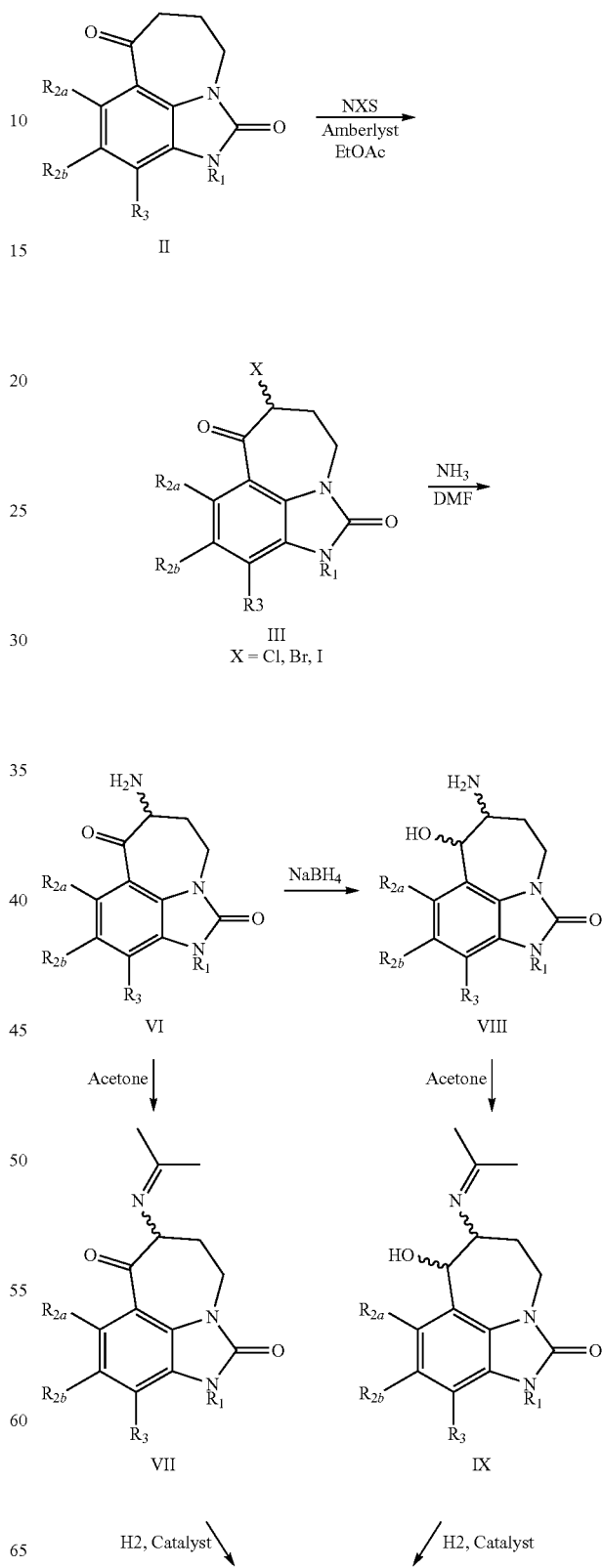

Additional embodiments of the method are given in Scheme 4 below.

-continued

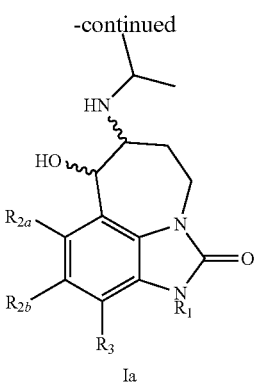

Ia

In an alternative embodiment, a method of preparing a compound of Formula Ia or a salt thereof

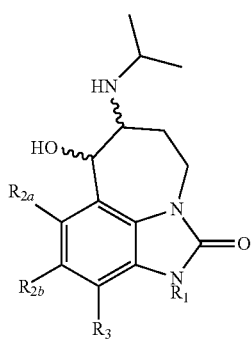

Ia comprising:
a. reacting a compound of Formula II

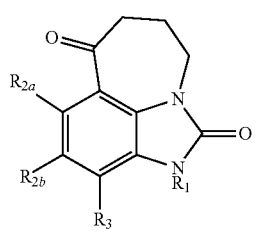

II with a halogenating agent to produce a compound of Formula III

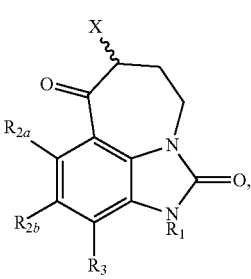

III wherein X is Cl, Br, or I;

b. reacting compound III with a compound of Formula A

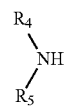

A wherein $R_4$ and $R_5$ of Formula A are hydrogen, to produce a compound of Formula VI;

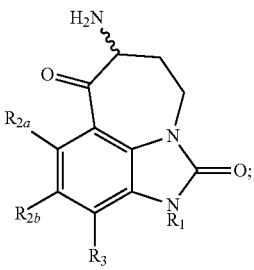

VI c. reacting the compound of Formula VI with acetone to form the compound of Formula VII

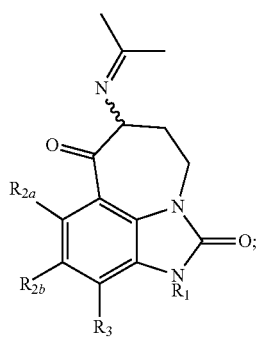

VII and
d. reacting the compound of Formula VII with a reducing agent to produce a compound of Formula Ia or a salt thereof

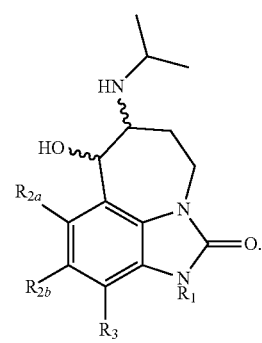

Ia

In yet another alternative embodiment, a method of preparing a compound of Formula Ia or a salt thereof

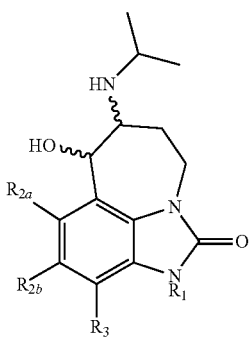

Ia comprising:
a. reacting a compound of Formula II

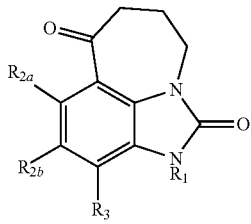

II with a halogenating agent to produce a compound of Formula III

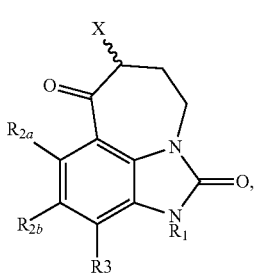

III wherein X is Cl, Br, or I;
b. reacting compound III with a compound of Formula A

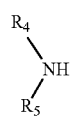

A wherein $R_4$ and $R_5$ of Formula A are hydrogen, to produce a compound of Formula VI;

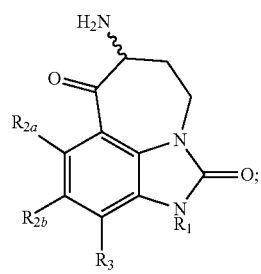

VI c. reacting the compound of Formula VI with a reducing agent to form the compound of Formula VIII

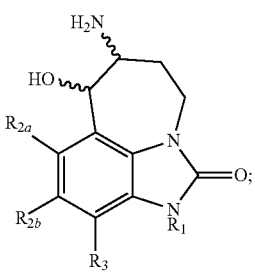

VIII d. reacting the compound of Formula VIII with acetone to produce a compound of Formula IX

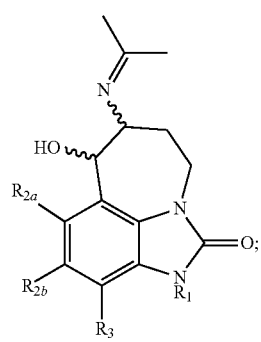

IX and
e. reacting the compound of Formula IX with a reducing agent to produce a compound of Formula Ia or a salt thereof

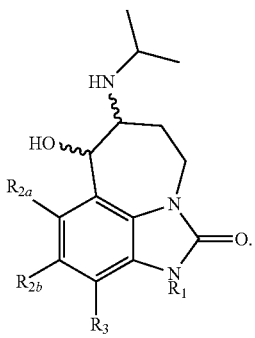

In another embodiment, the compound of Formula Ia is zilpaterol, wherein $R_1$-$R_3$ are hydrogen.

In another embodiment, the halogenating agent is is selected from N-chlorosuccinimide (NCS), N-bromosuccinimide (NBS), N-iodosuccinimide (NIS), bromine and iodine.

In another embodiment, the reducing agent is selected from sodium borohydride, potassium borohydride, lithium aluminum hydride and borane-tetrahydrofuran complex.

Other embodiments of the subject invention are the novel intermediate compounds 9a, 9b, 9c and 10. In compound 9a, X is Br; in compound 9b, X is Cl; and in compound 9c, X is I.

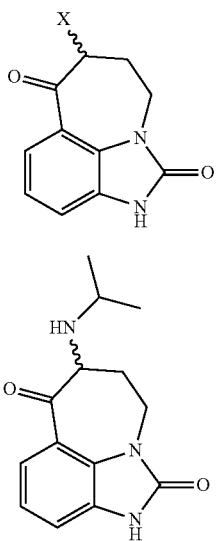

The inventors disclose herein an improved process for the preparation of (+/−)-zilpaterol (8). One advantage of the present invention is that it can shorten the manufacturing process of converting Intermediate 3 into (+/−)-zilpaterol by two processing steps or 40% fewer steps. Another advantage of the present invention is that it utilizes inexpensive and commercially available reagents. Yet another advantage of the present invention is that it does not require the use of the expensive catalytic reducing agents of the current manufacturing process. Still yet another advantage of the present invention over previous procedures is that it allows for modification of compound 3 which could produce various analogues of zilpaterol. Moreover, another object of the present invention is that it precedes through previously unknown intermediates 9 and 10, for which composition of matter is claimed. Combined these features may afford a scaleable and economical process suitable for large-scale production of (+/−)-zilpaterol (8) at reduced cost.

In another embodiment, it is envisioned the disclosed processes could be used to prepare other non zilpaterol beta-2-adrenoceptor agonists such as those disclosed in WO 2008/044127.

The term "alkyl" means a saturated straight or branched alkyl such as methyl, ethyl, propyl, or sec-butyl. Alternatively, the number of carbons in an alkyl can be specified. For example, "$C_{1-10}$alkyl" means an "alkyl" as described above containing 1, 2, 3, 4, 5, 6, 7, 8, 9 or 10 carbon atoms.

The term "$C_{2-10}$ alkenyl" means an unsaturated branched or unbranched hydrocarbon group having at least one double carbon-carbon (—C═C—) bond and containing 2, 3, 4, 5, 6, 7, 8, 9 or 10 carbon atoms. Example alkenyl groups include, without limitation, ethenyl, 1-propenyl, isopropenyl, 2-butenyl, 1,3-butadienyl, 3-pentenyl and 2-hexenyl, and the like.

The term "$C_{2-10}$ alkynyl" means an unsaturated branched or unbranched hydrocarbon group having at least one triple carbon-carbon (—C≡C—) bond and containing 2, 3, 4, 5, 6, 7, 8, 9 or 10 carbon atoms. Example alkynyl groups include, without limitation, ethynyl, 1-propynyl, 2-propynyl, 2-butynyl, 3-butynyl, 2-penten-4-ynyl, and the like.

The term "$C_{1-10}$ alkoxy" means an alkyl-O— group, where the term "alkyl" is defined herein. Example alkoxy groups include, without limitation, methoxy, ethoxy, propoxy (e.g., n-propoxy and isopropoxy), t-butoxy, and the like, The term "aryl" means phenyl, or phenyl substituted by $C_1$ to $C_6$ alkyl or "halo", where phenyl and halo are as defined herein.

The term "bromo" means the chemical element bromine.

The term "chloro" means the chemical element chorine.

The term "NXS" means N-chlorosuccinimide (NCS), N-bromosuccinimide (NBS), or N-iodosuccinimide (NIS), where X is Cl, Br or I, respectively.

Throughout the specification and the appended claims, a given chemical formula or name shall encompass all stereo and optical isomers and racemates thereof, as well as mixtures in different proportions of the separate enantiomers, where such isomers and enantiomers exist, as well as pharmaceutically acceptable salts thereof and solvates thereof such as for instance hydrates. Isomers can be separated using conventional techniques, e.g. chromatography or fractional crystallization. The enantiomers can be isolated by separation of a racemic mixture, for example, by fractional crystallization, resolution or high-performance (or -pressure) liquid chromatography (HPLC). The diastereomers can be isolated by separation of isomer mixtures, for instance, by fractional crystallization, HPLC or flash chromatography. The stereoisomers also can be made by chiral synthesis from chiral starting materials under conditions which will not cause racemization or epimerization, or by derivatization, with a chiral reagent. The starting materials and conditions will be within the skill of one skilled in the art. All stereoisomers are included within the scope of the invention.

EXAMPLES

Example 1

Preparation of 7-bromo-8,9-dihydro-2,9a-diazabenzo[cd]azulene-1,6(2H,7H)-dione (9a)

Ketone (3) (10.0 g, 49.4 mmol) was suspended in ethyl acetate (500 mL) and stirred at room temperature. N-Bromosuccinimide (previously recrystallized from hot water) (9.24 g, 51.9 mmol) and Amberlyst-15 (15 g) were then added and the reaction was stirred at 23° C. After 14 h, the reaction was filtered and the solid was washed with ethyl acetate (2×100 mL). The filtrate was discarded and the solid material added to hot methanol (~500 mL). The remaining Amberlyst-15 was removed from the methanol solution via filtration, and the methanol was removed by rotary evaporator to furnish 8.98 g of 9a (31.9 mmol, 65% yield) of a beige solid. $^1$H NMR (DMSO-$d_6$, 250 MHz): d 2.48-2.65 (m, 2H), 3.89-3.99 (m, 1H), 4.18-4.27 (m, 1H), 5.30 (dd, J=2.5 Hz, 12 Hz, 1H), 7.12 (t, J=7.5 Hz, 1H), 7.24 (d, J=7.4 Hz, 1H), 7.62 (d, J=7.5 Hz, 1H), 11.4 (br s, 1H); HRMS (ESI): calcd for $C_{11}H_9BrN_2O_2$[M+Na]=302.97. found 302.9721.

Example 2

Preparation of 7-chloro-8,9-dihydro-2,9a-diazabenzo[cd]azulene-1,6(2H,7H)-dione (9b)

The chloro ketone was prepared by the method described to prepare 9a using 1.00 g (4.94 mmol) of ketone 3, N-chlorosuccinimide (990 mg, 7.41 mmol), Amberlyst-15 (1.5 g), and 50 mL of ethyl acetate. The chloro ketone product 9b was isolated in 72% yield (842.5 mg, 3.56 mmol) as a light yellow solid. $^1$H NMR (DMSO d6, 250 MHz): d 2.51-2.71 (m, 2H), 3.84-3.98 (m, 1H), 3.99-4.09 (m, 1H), 5.28 (dd, J=2.5 Hz, 7.5 Hz, 1H), 7.10 (t, J=7.5 Hz, 1H), 7.24 (d, J=7.4 Hz, 1H), 7.58 (d, J=7.5 Hz, 1H), 11.4 (br s, 1H).

Example 3

7-iodo-8,9-dihydro-2,9a-diazabenzo[cd]azulene-1,6 (2H,7H)-dione (9c)

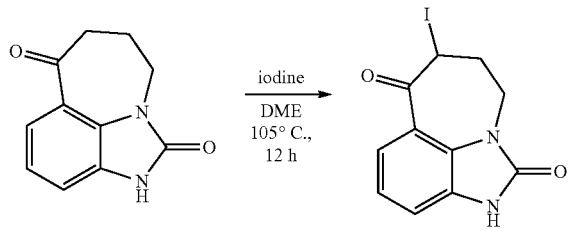 [SMILES: O=C1CCCn2c(=O)[nH]c3cccc1c32 ; O=C1c2cccc3[nH]c(=O)n(c23)CCC1I]

Procedure: Into a 4 mL vial equipped with a stir bar was added buzolinone (0.101 g; 0.50 mmol), iodine (0.63 g; 2.5 mmol; 5 equiv), and 1,2-dimethoxyethane (2.5 mL). The vial is capped and the deep red solution is stirred for 12 h at 105° C. The reaction mixture is diluted with $CH_2Cl_2$ (50 mL) and washed with sat. $Na_2S_2O_{3(aq)}$ (50 mL). The aqueous layer is separated and extracted with $CH_2Cl_2$ (2×50 mL). The combined organic layers are dried over $Na_2SO_4$, filtered, and concentrated to yield $C_{11}H_9IN_2O_2$ (0.153 g; 94%) as a yellow solid. $^1$H NMR (DMSO-$d^6$, 400 MHz): δ 2.15-2.21 (m, 1H), 2.33-2.40 (m, 1H), 3.84-3.91 (m, 1H), 4.32-4.37 (m, 1H), 5.42-5.43 (m, 1H), 7.08 (m, 1H), 7.23 (dd, J=7.5, 1.0 Hz, 1H), 7.57 (dd, J=8.2, 1.0 Hz), 11.4 (br s, 1H); HRMS (ESI): calcd for $C_{11}H_9IN_2O_2$ [M+Na]=350.9601. found 350.9588.

Example 4

Preparation of (6R,7R)-rel-4,5,6,7-tetrahydro-7-hydroxy-6-[(1-methylethyl)amino]-imidazo[4,5,1-jk] [1]benzazepin-2(1H)-one (8) through (10)

To a small vial equipped with a stir bar was added bromoketone (9a) (141 mg, 0.500 mmol). The vial was capped with a septum and backfilled with argon three times. Dry, distilled dimethylforamide (DMF) (1.0 mL) was added to the flask and the reaction mixture was stirred. Isopropylamine (0.46 mL, 5.00 mmol) was added and the reaction was stirred at 23° C. for 15 min. After this time, sodium borohydride (38 mg, 1.0 mmol) was added and the reaction was stirred for 15 min. The vial was transferred to a 50-mL round-bottom flask, and the flask was placed under high vacuum. Upon removal of all volatile components, the remaining crude residue was dissolved in 10% methanol/dichloromethane (MeOH/DCM), and silica gel was added. The solvent was then removed and the silica gel containing the product was loaded onto a silica gel column and purified using 20% MeOH/DCM with 1% $NEt_3$ ($R_f$=0.2). The free base zilpaterol (8) was isolated in 52% yield (68 mg, 0.26 mmol) as a white solid. $^1$H NMR ($CD_3OD$, 400 MHz): 1.38 (d, J=6.4 Hz, 3H), 1.43 (d, J=6.4 Hz, 3H), 2.09☐2.13 (m, 1H), 2.51-2.68 (m, 1H), 3.60-3.63 (m, 2H), 3.89-3.96 (m, 1H), 4.4.23-4.28 (m, 1H), 4.97 (d, J=8.4 Hz, 1H), 7.08-7.16 (m, 2H), 7.33 (d, J=7.6 Hz, 1H); HRMS (ESI): calcd for $C_{14}H_{19}N_3O_2$ [M+]=261.15. found 261.9500.

The words "process" and "method" are used interchangeably in this patent. All references cited in this patent are incorporated by reference into this patent. The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

The invention claimed is:
1. A method of preparing a compound of Formula I or a salt thereof

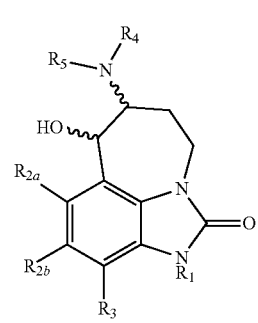

comprising:
a. reacting a compound of Formula II

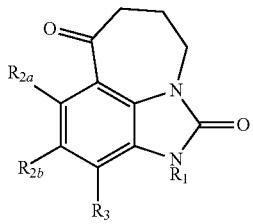

with a halogenating agent to produce a compound of Formula III

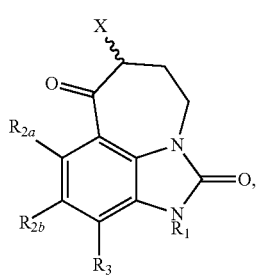

wherein X is Cl, Br, or I;
b. reacting compound III with a compound of Formula A

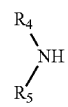

to produce a compound of Formula IV;

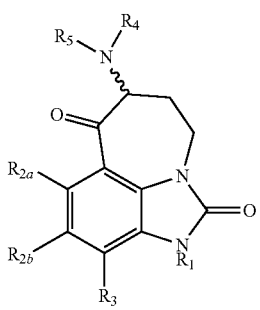

and
c. reacting compound IV with a reducing agent to produce a compound of Formula I wherein:
$R_1$ is selected from hydrogen, amino, alkyl, alkenyl, alkynyl, aryl, or benzyl, and wherein for each alkyl, alkenyl, alkynyl, aryl, and benzyl may be substituted or unsubstituted;
$R_{2a}$ and $R_{2b}$ are the same or different and are each independently selected from hydrogen, halogen, hydroxyl, amino, alkyl, alkenyl, alkynyl, aryl, benzyl, alkoxy, alkylthioxy, alkyl sulfonyl, alkyl sulfoxy, or alkyl thio, and wherein for each alkyl, alkenyl, alkynyl, aryl, benzyl, alkoxy, alkylthioxy, alkyl sulfonyl, alkyl sulfoxy, and alkyl thio may be substituted or unsubstituted;
$R_3$ is selected from hydrogen, halogen, hydroxyl, amino, alkyl, alkenyl, alkynyl, aryl, benzyl, alkoxy, alkylthioxy, alkyl sulfonyl, alkyl sulfoxy, or alkyl thio, and wherein for each alkyl, alkenyl, alkynyl, aryl, benzyl, alkoxy, alkylthioxy, alkyl sulfonyl, alkyl sulfoxy, and alkyl thio may be substituted or unsubstituted; and
$R_4$ and $R_5$ are independently selected from hydrogen, amino, alkyl, alkenyl, alkynyl, aryl, or benzyl, and wherein for each alkyl, alkenyl, alkynyl, aryl, and benzyl, may be substituted or unsubstituted; or $R_4$ and $R_5$ may be taken together to form a cyclic substituent, wherein the cyclic substituent may be aromatic or non aromatic and may further include one or more additional hetero atoms selected from O, S and N.

2. The method of claim 1, wherein the reaction of part b and the reaction of part c are conducted in situ and compound IV is not isolated.

3. The method of claim 1, wherein $R_1$, $R_{2a}$, $R_{2b}$, $R_3$ and $R_5$ are hydrogen.

4. The method of claim 1, wherein $R_4$ is isopropyl.

5. A method of preparing a compound of Formula I or a salt thereof

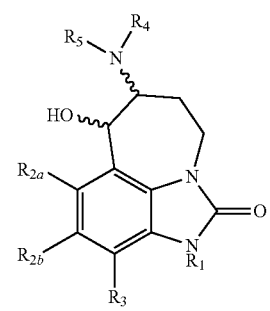

comprising reacting a compound of Formula III

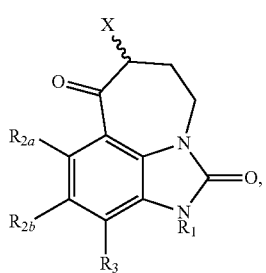

wherein X is Cl, Br, or I;

with a compound of Formula A

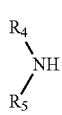

to produce a compound of Formula IV;

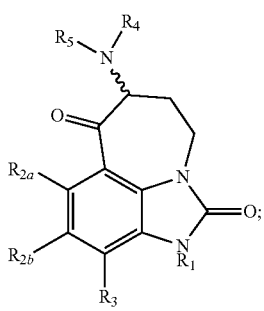

and
reacting compound IV with a reducing agent to produce a compound of Formula I;
wherein $R_1$, $R_{2a}$, $R_{2b}$, $R_3$, $R_4$ and $R_5$ are defined as in claim 1.

6. A method of preparing a compound of Formula I or a salt thereof

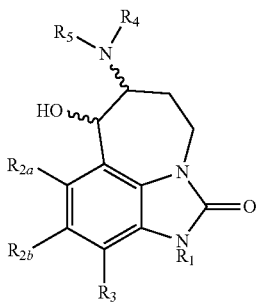

comprising reacting a compound of Formula IV

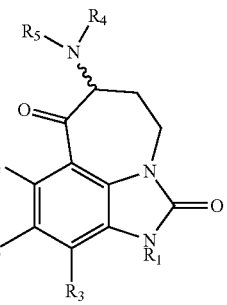

with a reducing agent to produce a compound of Formula I, wherein $R_1$, $R_{2a}$, $R_{2b}$, $R_3$, $R_4$ and $R_5$ are defined as in claim 1.

7. The method of claim 1, wherein the reducing agent is selected from sodium borohydride, potassium borohydride, lithium aluminum hydride and borane-tetrahydrofuran complex.

8. The method of claim 7 wherein the reducing agent is $NaBH_4$.

9. The method of claim 1, wherein the halogenating agent is selected from N-chlorosuccinimide (NCS), N-bromosuccinimide (NBS), N-iodosuccinimide (NIS), bromine and iodine.

10. The method of claim 9, wherein the halogenating agent is N-bromosuccinimide (NBS).

11. The method of claim 9, wherein the halogenating agent is bromine.

12. The method of claim 9, wherein the halogenating agent is N-chlorosuccinimide (NCS).

13. The method of claim 9, wherein the halogenating agent is iodine.

* * * * *